United States Patent [19]
Kohayakawa

[11] Patent Number: 5,090,798
[45] Date of Patent: Feb. 25, 1992

[54] APPLIED INTENSITY DISTRIBUTION CONTROLLING APPARATUS

[75] Inventor: Yoshimi Kohayakawa, Yokohama, Japan

[73] Assignee: Canon Kabushiki Kaisha, Tokyo, Japan

[21] Appl. No.: 664,431

[22] Filed: Mar. 4, 1991

Related U.S. Application Data

[63] Continuation of Ser. No. 453,209, Dec. 27, 1989, abandoned, which is a continuation of Ser. No. 184,194, Apr. 21, 1988, abandoned.

[30] Foreign Application Priority Data

Apr. 27, 1987 [JP] Japan .............................. 62-103624
May 22, 1987 [JP] Japan .............................. 62-125390

[51] Int. Cl.$^5$ .............................................. A61B 3/10

[52] U.S. Cl. ......................................... 351/221; 606/5; 128/395

[58] Field of Search ............................. 351/221, 233; 128/303.1, 303.14, 395; 606/3, 5

[56] References Cited

U.S. PATENT DOCUMENTS 4,665,913  5/1987  L'Esperance, Jr. .............. 128/303.1
4,732,148  3/1988  L'Esperance ..................... 351/221

*Primary Examiner*—Paul M. Dzierzynski
*Attorney, Agent, or Firm*—Fitzpatrick, Cella, Harper & Scinto

[57] ABSTRACT

An applied intensity distribution controlling apparatus having an optical system passing an applied light beam therethrough and including a cylindrical lens, and an opening member in which the passage width of the applied light beam in the generatrix direction of the cylindrical lens forms a predetermined distribution.

17 Claims, 4 Drawing Sheets

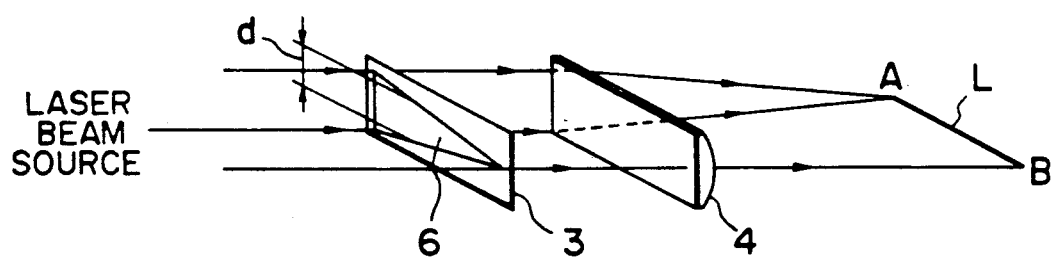
FIG. IA
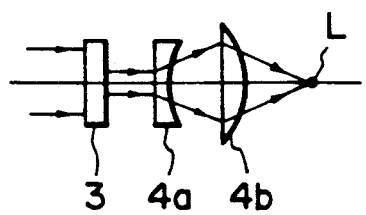
FIG. IB
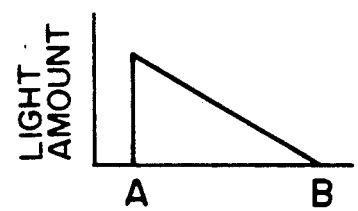
FIG. 2
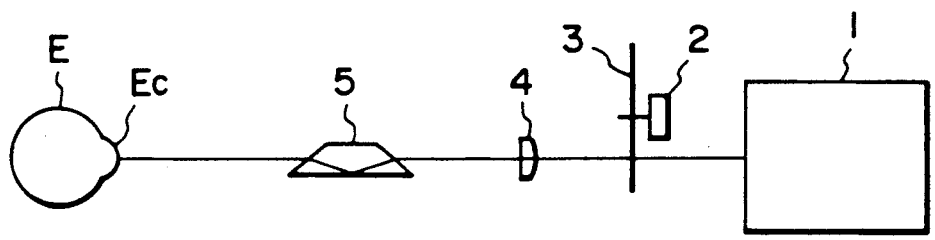
FIG. 3
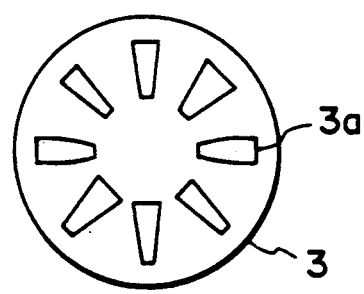
FIG. 4
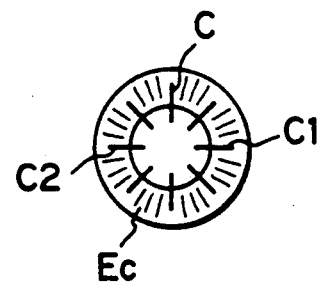
FIG. 5

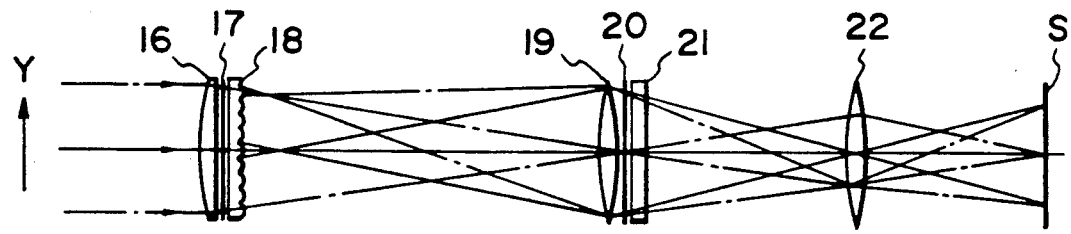
F I G. 8A
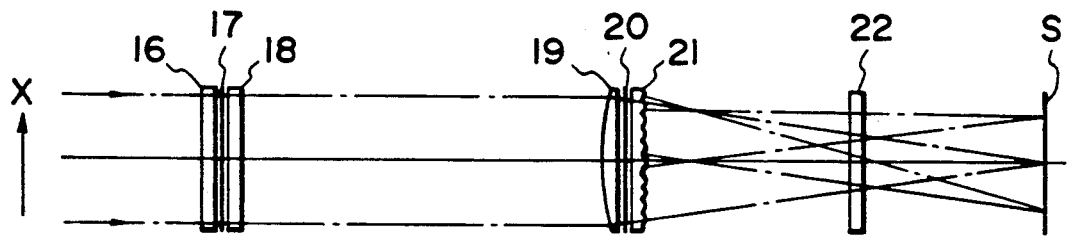
F I G. 8B
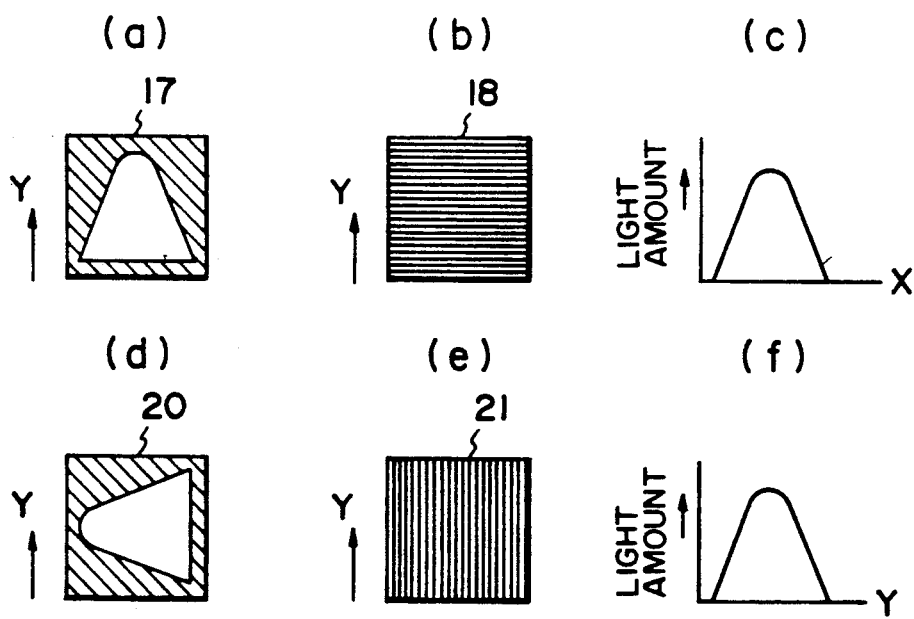
F I G. 9

APPLIED INTENSITY DISTRIBUTION CONTROLLING APPARATUS

This application is a continuation of application Ser. No. 07/453,209, filed Dec. 27, 1989, now abandoned, which is a continuation of application Ser. No. 184,194, filed Apr. 21, 1988, now abandoned.

BACKGROUND OF THE INVENTION

1. Field of the Invention

This invention relates to an apparatus which can simply and stably control the intensity distribution of an applied light as a desired intensity distribution and which can be applied, for example, to an apparatus for treating the cornea of an eye to be examined.

2. Related Background Art

In recent years, in the corneal refraction correcting operations, it has been practice to apply a laser beam such a as an excimer laser to the cornea of an eye to be examined to thereby incise radially the surface of the marginal portion of the cornea and adjust the curvature of the central portion of the cornea. In such laser cornea treating apparatus, the laser beam is made into a linear beam by the use of a cylindrical lens or the like and the linear beam is applied to the cornea surface of the eye to be examined, thereby accomplishing a cornea incision operation.

However, in the above-described apparatus, when incising the surface of the marginal portion of the cornea, it is difficult to incise each portion of the cornea to a desired depth because neither is the illumination distribution of the linear laser beam uniform nor is the thickness of the cornea of the eye to be examined uniform.

In the prior art, to freely control the distribution of the applied quantity of light on the irradiated surface by a light beam emitted from a light source, several kinds of filters having various density distributions must be prepared and the intensity distribution must be adjusted. Filters having such density distributions are generally made by metal deposition or optical etching or the like, but such methods of making filters are considerably complex and take much time and are inaccurate in density distribution, and it is often the case that a desired light-quantity distribution is not obtained even if a light beam is passed through the filters.

Also, where a powerful pulse laser such as an excimer laser is applied, for example, to a cornea shaping operation or the like, if the density distributions of the filters are inaccurate, no precise light-quantity distribution is obtained and further, the filters may possibly be destroyed, that is, the filters lack in durability and it is not only difficult but also dangerous to use such filters in the cornea shaping which requires precise control of a laser beam.

In U.S. Pat. No. 4,665,913, it is disclosed to scan a spot light beam on the cornea of an eye to be examined to thereby obtain a desired intensity distribution. However, the light scanning requires a varying amount of time, and this leads to the necessity of a cumbersome operation of temporarily stopping the application of the laser beam when the eye to be examined has moved and again applying the laser beam after alignment.

SUMMARY OF THE INVENTION

It is an object of the present invention to provide an applied intensity distribution controlling apparatus which can make the intensity distribution of an applied light such as a laser beam into a desired intensity distribution on an irradiated surface.

It is also an object of the present invention to provide an apparatus which can stably treat the cornea of an eye to be examined by the use of a laser beam such as an excimer laser.

BRIEF DESCRIPTION OF THE DRAWINGS

Figure 1A shows a first embodiment of the present invention.

FIG. 1B shows a modification of the FIG. 1A embodiment.

FIG. 2 is a graph showing the illumination distribution of a linear laser beam in the first embodiment.

FIG. 3 shows a laser cornea treating apparatus to which the first embodiment is applied.

FIG. 4 is a front view of a turret type opening plate.

FIG. 5 illustrates incision lines.

FIG. 8A shows the construction of a third embodiment of the present invention in a plane y.

FIG. 8B shows the construction of the third embodiment in a plane x.

FIGS. 9(a) and (d) are front views of opening plates.

FIGS. 9(b) and (e) are front views of cylindrical lens arrays.

FIGS. 9(c) and (f) are graphs of light-quantity distributions.

DESCRIPTION OF THE PREFERRED EMBODIMENTS

Figures 10, 11:
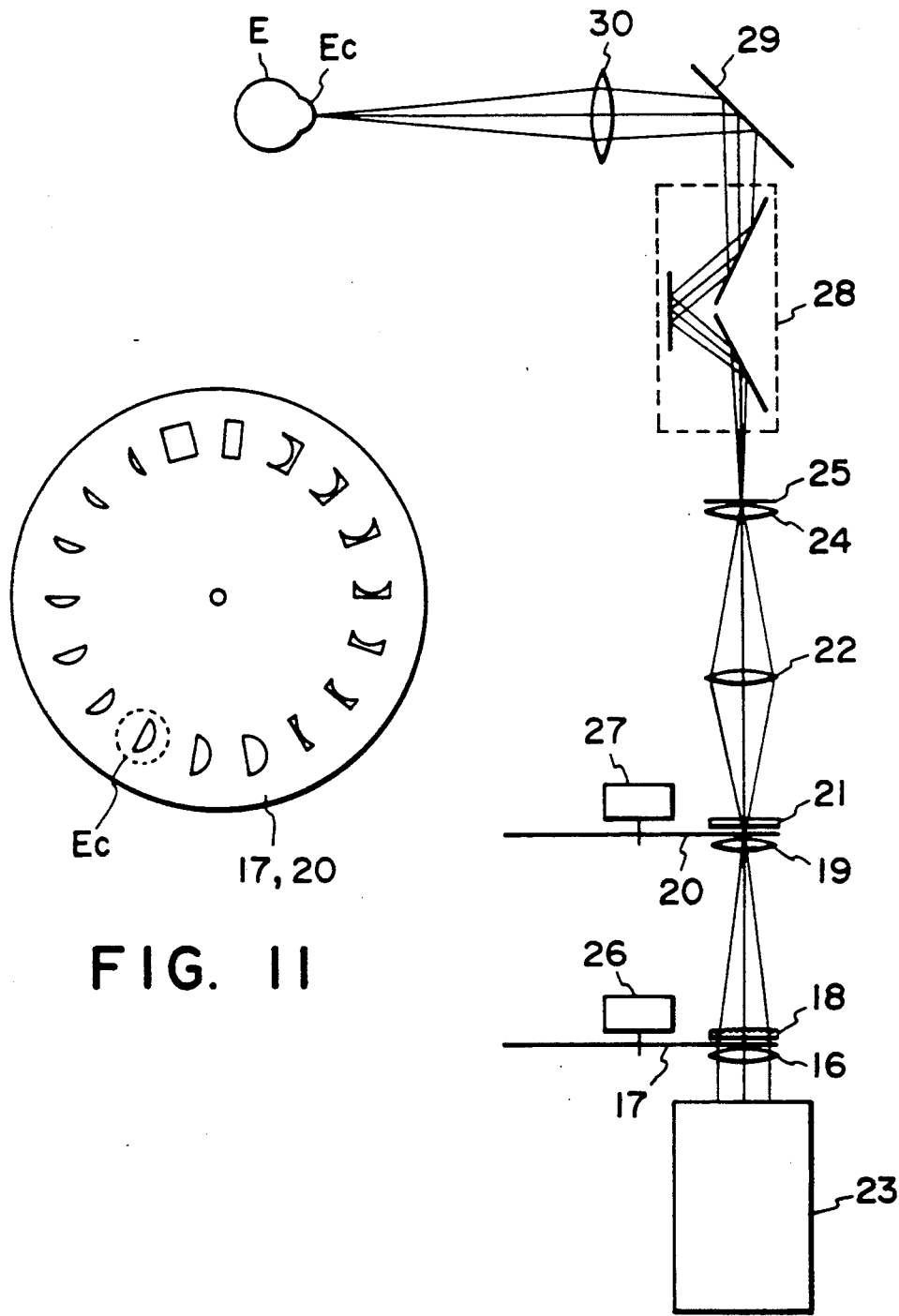
FIG. 10 shows the construction of a laser cornea treating apparatus to which the third embodiment is applied.
FIG. 11 is a front view of an opening plate having a plurality of openings.

FIG. 1A shows a first embodiment of the present invention which is capable of accomplishing one-dimensional illumination distribution control, in which a parallel laser beam emitted from a laser source passes through an opening plate 3 having an opening 6 whose opening width d varies in a direction AB in a plane perpendicular to the optic axis as shown, for example, in FIG. 1A, and a cylindrical lens 4 provided with a generatrix direction in the direction AB, and is condensed as a linear laser beam on a segment L. The illumination distribution of this linear beam is an illumination distribution proportional to the opening width d as shown in FIG. 2.

That is, the laser beam passed through the portion of the opening 6 in which the opening width d is great has a great quantity of light and therefore the illumination thereof when it is condensed as the linear beam becomes strong, and the laser beam passed through the portion of the opening 6 in which the opening width d is small has a small quantity of light and therefore the illumination thereof when it is condensed as the linear beam becomes weak. The segment L, in the case of a cornea treating apparatus, corresponds to the segment on the cornea surface.

As a modification, design may be made such that the parallel beam passed through the opening plate 3 is condensed on the segment L through a concave cylindrical lens 4a and a convex cylindrical lens 4b whose generatrix directions are parallel to each other, as shown in FIG. 1B.

FIG. 3 shows the construction of a laser cornea treating apparatus to which the above-described first embodiment is applied, in which a turret type rotatable opening plate 3 is mounted on an electric motor 2, a cylindrical lens 4 and a rotator 5 which is an image rotator having an odd number of reflecting surfaces are successively disposed along the optical path of a laser beam emitted from a laser source 1. The turret type opening plate 3, as shown in FIG. 4, is provided with a plurality of openings 3a whose opening width is not constant, and by rotating the turret type opening plate 3 by the electric motor 2, a suitable opening 3a can be selected.

In the thus constructed laser cornea treating apparatus, the laser beam emitted from the laser source 1 passes through one of the plurality of openings 3a provided in the turret type opening plate 3 to the cylindrical lens 4 and is condensed as a linear laser beam. This linear laser beam has its direction rotated by the rotator 5, and when it is applied onto the cornea Ec of an eye E to be examined and forms an incision line C on the cornea Ec as shown in FIG. 5.

As the illumination of the linear beam is stronger when the incision of the cornea Ec is effected, the depth to which the cornea is incised per unit time becomes greater and therefore, if the opening width d of the opening 3a is set in accord with the thickness of the cornea Ec of the eye E to be examined to which the linear laser beam is applied, it will become possible to incise the cornea Ec in an optimum condition.

In the above-described apparatus, the laser beam is directly applied to the opening 3a, but where the cross-sectional area of the laser beam is large as compared with the opening 3a, if an optical system comprising a combination of a convex lens and a concave lens is provided between the laser source 1 and the turret type opening plate 3 so that the laser beam may be applied to the opening 3a after the diameter of the laser beam is reduced in advance to the degree of the opening 3a, the laser beam can be utilized effectively.

Also, where the quantity of light of the laser beam is sufficiently great, two openings, instead of a single opening 3a, may be provided radially of the turret type opening plate 3, whereby it will become possible to form at one time two incision lines C1 and C2 which are in symmetric positional relationship on the cornea Ec of the eye E to be examined. In such a case, the turret type opening plate 3 may be rotated so that two desired radial openings may lie at a position corresponding to the cornea Ec of the eye E to be examined.

Figure 6A:
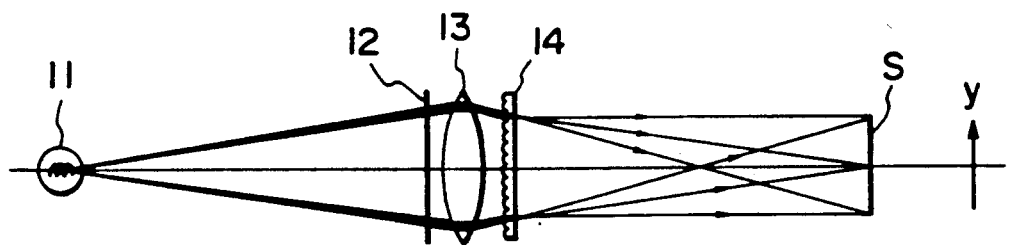
FIG. 6A shows a second embodiment of the present invention.

FIG. 6A shows a second embodiment of the present invention, in which an opening plate 12, a toric lens 13 and a cylindrical lens array 14 are disposed in succession from a light source 11 side. The light source 11 may be a laser source such as an excimer laser.

Figure 7:
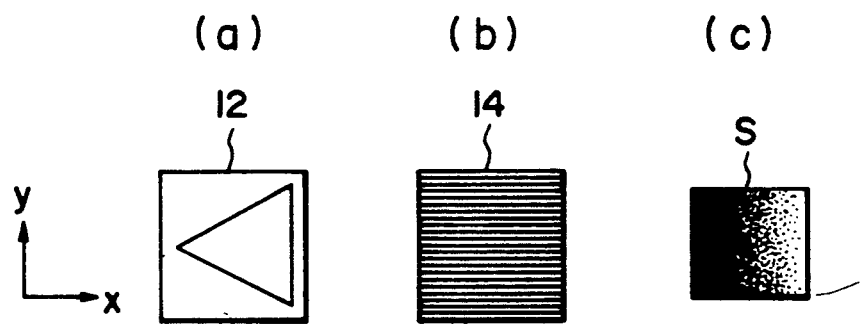
FIG. 7(a) is a front view of an opening plate.
FIG. 7(b) is a front view of a cylindrical lens array.
FIG. 7(c) shows the light-quantity distribution of an applied light beam.

A light beam emitted from the light source 11 passes through the opening plate 12 having a triangular opening as shown, for example, in FIG. 7(a) and is condensed by the toric lens 13 having a strong condensing property in a direction y but exhibiting only a weak condensing property in a direction x. The light beam then enters the cylindrical lens array 14 comprising a number of small cylindrical lenses having their generatrix directions in the direction x and densely arranged in the direction y, as shown in FIG. 7(b). The refraction in the direction y by the cylindrical lens array 14 is made random and therefore, the shape of an image formed on an irradiated surface S is such that shown in FIG. 7(c), the intensity distribution has a gradient in the direction x and is uniformly averaged in the direction y.

Figure 6B:
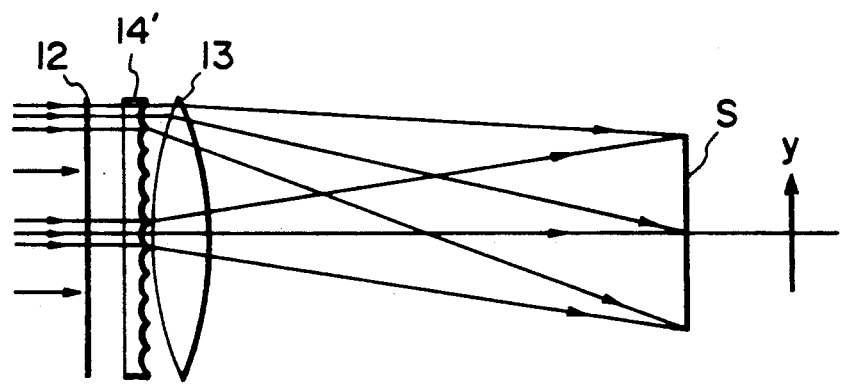
FIG. 6B shows a modification of the FIG. 6A embodiment.

Alternatively, design may be made such that as shown in FIG. 6B, a parallel light beam is applied to the opening plate 12 having a triangular opening and the intensity distribution as shown in FIG. 7(c) is formed on the irradiated surface S through a concave cylindrical lens array 14' in which the focus of each lens is on the opening plate 12 and a toric lens 13.

In FIGS. 6A and 6B, the toric lens as a condensing optical system causes the principal ray of the applied light beam passed through each cylindrical lens of the cylindrical lens array 14, 14' to be condensed to the irradiated surface S.

In the case of the cornea treating apparatus, the irradiated surface S is the cornea surface.

FIGS. 8A and 8B show a third embodiment which is capable of accomplishing two-dimensional illumination distribution control, FIG. 8A showing the construction in a plane y, and FIG. 8B showing the construction in a plane x. The light beam emitted from a light source is, for example, a parallel laser beam, and a first cylindrical lens 16 having a condensing property only in the direction y, a first opening plate 17, a first cylindrical lens array 18 serving to uniformly average the light in the direction y and having its generatrix directions in the direction x, a toric lens 19 having different refractive powers in the direction x and the direction y, a second opening plate 20, a second cylindrical lens array 21 serving to uniformly average the light in the direction x and having its generatrix directions in the direction y, a second cylindrical lens 22 having a condensing property only in the direction y and an irradiated surface S are arranged in the named order. The spacing between the first cylindrical lens 16 and the second opening plate 20 is equal to the focal length of the first cylindrical lens 16, and the toric lens 19 has the function of a field lens in the direction y and is adapted to image the first cylindrical lens array 18 near the second cylindrical lens 22. The first opening plate 17 and the second opening plate 20 are disposed as shown in FIGS. 9(a) and (d), respectively, and the first cylindrical lens array 18 and the second cylindrical lens array 21 are installed in such a manner that the directions in which small cylindrical lenses are arranged differ by 90° as shown in FIGS. 9(b) and (e).

With such a construction, as shown in FIGS. 8A and 8B, the light beam is made into a light beam having an illumination distribution as shown in FIG. 9(c) which conforms to the shape of the opening of the first opening plate 17, by the first cylindrical lens 16, the first opening plate 17 and the first cylindrical lens array 18. The light beam by the second opening plate 20 and the second cylindrical lens array 21 is given an illumination distribution as shown in FIG. 9(f) which conforms to the shape of the opening, on the irradiated surface S. The image in the direction y refracted by the toric lens 19 is formed near the second cylindrical lens 22 and finally, there is formed on the irradiated surface S an image having certain predetermined illumination distributions in the directions x and y in conformity with the shapes of the openings of the two opening plates 17 and 20.

Thus, the illumination distribution in the direction x is determined by the shape of the opening of the first opening plate 17 and the illumination distribution in the direction y is determined by the shape of the opening of the second opening plate 20 and therefore, by changing these two opening plates 17 and 20 into suitable shapes, various two-dimensional applied light-quantity distributions can be freely created. The toric lens 19 may be two cylindrical lenses of different refractive powers, or may be a cylindrical lens having a condensing property only in the direction x if the size of the second cylindrical lens 22 is sufficiently large. In the case of the cornea treating apparatus, the irradiated surface S is the cornea surface.

A laser cornea forming operation apparatus for the eye E to be treated as shown, for example, in FIG. 10 is conceivable as an application of such two-dimensional applied light-quantity control means. A light beam emitted from a laser oscillation device 23 such as an excimer laser passes to a field lens 24 and a circular opening plate 25 through entirely the same process as in the previously described third embodiment. The circular opening plate 25 is conjugate with the cornea Ec and corresponds to the surface S in FIG. 8. A first opening plate 17 and a second opening plate 20 presents a disc-like shape having a number of openings of various shapes as shown in FIG. 11, and may be rotated by electric motors 26 and 27, respectively, so that an opening of any desired shape can be selected. An image rotator 28, a mirror 29 and an objective lens 30 are successively disposed rearwardly of the opening plate 25. The objective lens 30 images the surface of the circular opening plate 25 on the cornea Ec.

The image rotator 28 is for determining the astigmatic angle and can be rotated about the optic axis to thereby project the light-quantity distribution on the circular opening plate 25 onto the cornea Ec of the eye E to be treated at a predetermined angle, and the mirror 29 and the objective lens 30 are disposed so as to direct the light beam given a predetermined angle by the image rotator 28 onto the cornea Ec.

For example, when near-sightedness is to be corrected, the curvature of the cornea Ec is made gentler and therefore, there may be provided a light-quantity distribution which is strong at the center of the cornea and weak in the marginal portion thereof, and in the first and second opening plates 17 and 20, an arcuate opening shape in which the opening width is greater in the central portion than in the marginal portion may be selected. An opening of appropriate shape may likewise be selected for the correction of far-sightedness or astigmatism, and it becomes possible to easily obtain a light-quantity distribution necessary for refraction correction and thus, a highly reliable surgical operation becomes possible by a stable operation. As regards the first opening plate 17 and the second opening plate 20, for example, the light-quantity distribution in the horizontal direction can be controlled by the opening shape of the first opening plate 17 and the light-quantity distribution in the vertical direction can be controlled by the opening shape of the second opening plate 20.

I claim:

1. A light intensity distribution controlling apparatus provided with:

an optical system including a cylindrical lens and passing an applied light beam therethrough and imaging the light beam onto a projection plane provided substantially on a focal plane of said cylindrical lens; and an opening member in which the passage width of the applied light flux has a predetermined non-uniform distribution along the direction of the axis of said cylindrical lens, wherein an intensity distribution of the imaged light beam on the projection plane in the direction of said axis is non-uniform and the same as the distribution of the passage width of the opening member.

2. An applied intensity distribution controlling apparatus according to claim 1, wherein the applied light beam enters said opening member as a parallel light beam.

3. An applied intensity distribution controlling apparatus according to claim 1, wherein the applied light beam is a laser beam.

4. An applied intensity distribution controlling apparatus according to claim 1, wherein said opening member is interchangeable with an opening member in which the distribution of the passage width of the applied light beam in said generatrix direction differs.

5. A light intensity distribution controlling apparatus provided with:

a cylindrical lens array passing an applied light beam therethrough and having a plurality of cylindrical lenses the axes of which are parallel with each other;

an opening member in which the passage width of the applied light flux has a non-uniform distribution along said axes of said cylindrical lenses; and a condensing optical system for condensing the principal ray of the applied light beam passed through each cylindrical lens of said cylindrical lens array, said condensing optical system having a substantial refractive power in the direction perpendicular to said axes of said cylindrical lenses.

6. An applied intensity distribution controlling apparatus according to claim 5, wherein said condensing optical system is provided with a toric lens having a weak condensing property in said generatrix direction and having a strong condensing property in a direction orthogonal thereto.

7. An applied intensity distribution controlling apparatus provided with:

a first cylindrical lens array passing an applied light beam therethrough and including a plurality of cylindrical lenses whose generatrix directions are parallel to a first direction;

a first opening member in which the passage width of the applied light beam in the generatrix direction of said first cylindrical lens array forms a predetermined distribution;

a first condensing optical system for condensing the principal ray of the applied light beam passed through each cylindrical lens of said first cylindrical lens array on a first irradiated surface in a second direction perpendicular to said first direction;

a second cylindrical lens array disposed near said first irradiated surface for passing the applied light beam therethrough and including a plurality of cylindrical lenses whose generatrix directions are parallel to said second direction;

a second opening member disposed near said first irradiated surface and in which the passage width of the applied light beam in the generatrix direction of said second cylindrical lens array forms a predetermined distribution; and a second condensing optical system for condensing said first irradiated surface on a second irradiated surface in said second direction and condensing the principal ray of the applied light beam passed through each cylindrical lens of said second cylindrical lens array on said second irradiated surface in said first direction.

8. An applied intensity distribution controlling apparatus according to claim 7, wherein said first condensing optical system is provided with a cylindrical lens whose generatrix direction is said first direction.

9. An applied intensity distribution controlling apparatus according to claim 8, wherein said second condensing optical system is provided with a cylindrical lens whose generatrix direction is said first direction, and a field lens for projecting said first cylindrical lens array near said cylindrical lens.

10. A cornea treating apparatus provided with:
a laser source for irradiating the cornea surface of an eye to be examined;
an optical system passing an applied laser beam therethrough and imaging the light beam onto the surface of the cornea, said optical system including a cylindrical lens, the focal plane of said cylindrical lens being provided substantially on the cornea surface; and
an opening member in which the passage width of the applied light flux has a predetermined non-uniform distribution along the direction of the axis of said cylindrical lens, wherein an intensity distribution of the imaged light beam on the cornea surface in the direction of said axis is non-uniform and the same as the distribution of the passage width of the opening member.

11. A cornea treating apparatus provided with:
a laser source for irradiating the cornea surface of an eye to be examined;
a cylindrical lens array passing an applied light beam therethrough and having a plurality of cylindrical lenses the axes of the which are parallel with each other;
an opening member in which the passage width of the applied light flux has a non-uniform distribution along said axes of said cylindrical lenses; and
a condensing optical system for condensing the principal ray of the applied light beam passed through each cylindrical lens of said cylindrical lens array, said condensing optical system having a substantial refractive power in a direction perpendicular to said axes of said cylindrical lenses.

12. A cornea treating apparatus provided with:
a laser source for irradiating the cornea surface of an eye to be examined;
a first cylindrical lens array passing an applied laser beam therethrough and including a plurality of cylindrical lenses whose generatrix directions are parallel to a first direction;
a first opening member in which the passage width of the applied laser beam in the generatrix direction of said first cylindrical lens array forms a predetermined distribution;
a first condensing optical system for condensing the principal ray of the applied laser beam passed through each cylindrical lens of said first cylindrical lens array on a first irradiated surface in a second direction perpendicular to said first direction;

a second cylindrical lens array disposed near said first irradiated surface for passing the applied laser beam therethrough and including a plurality of cylindrical lenses whose generatrix directions are parallel to said second direction;
a second opening member disposed near said first irradiated surface and in which the passage width of the applied laser beam in the generatrix direction of said second cylindrical lens array forms a predetermined distribution; and
a second condensing optical system for condensing said first irradiated surface on a second irradiated surface in said second direction and condensing the principal ray of the applied laser beam passed through each cylindrical lens of said second cylindrical lens array on the cornea surface which is said second irradiated surface in said first direction.

13. A light intensity distribution controlling apparatus provided with:
an optical system including a cylindrical lens and transmitting light flux therethrough and imaging the light flux onto a projection plane provided substantially on a focal plane of said cylindrical lens, said optical system having a substantial refractive power in a predetermined direction and having a negligible refractive power in the direction perpendicular to the predetermined direction; and
an opening member in which the passage width of the applied light flux has a predetermined non-uniform distribution along the direction perpendicular to said predetermined direction, wherein an intensity distribution of the imaged light beam on the projection plane in a direction perpendicular to said predetermined direction is non-uniform and the same as the distribution of the passage width of the opening member.

14. A cornea treating apparatus provided with:
a laser source for irradiating the cornea surface of an eye to be examined;
an optical system including a cylindrical lens and transmitting the irradiating laser beam therethrough and imaging the light flux onto the surface of the cornea, said optical system having a substantial refractive power in a predetermined direction and having a negligible refractive power in the direction perpendicular to said predetermined direction, the focal plane of said cylindrical lens being provided substantially on the cornea surface; and
an opening member in which the passage width of the applied laser beam has a predetermined non-uniform distribution along the direction perpendicular to said predetermined direction, wherein an intensity distribution of the imaged light beam on the cornea surface in the direction of said axis is non-uniform and the same as the distribution of the passage width of the opening member.

15. A light density distribution controlling apparatus, comprising:
an asymmetrical condensing optical system whose refractive powers are different in perpendicularly crossing meridian directions, said optical system having a substantial refractive power in a predetermined direction and transmitting a light flux therethrough, thereby imaging the light flux onto a projection plane, the condensing plane of said optical system being provided substantially on the projection plane;

an opening member in which the passage width of the applied light flux has a predetermined non-uniform distribution along one direction, wherein an intensity distribution perpendicular to said predetermined direction is non-uniform in the same manner as the distribution of the passage width of the opening member.

16. An apparatus to claim 15, further comprising a laser light source for providing a laser light flux.

17. An apparatus according to claim 16, wherein said projection plane is a surface of a cornea of an eye to be examined by said apparatus.

* * * * *

UNITED STATES PATENT AND TRADEMARK OFFICE
CERTIFICATE OF CORRECTION

PATENT NO. : 5,090,798

DATED : February 25, 1992

INVENTOR(S) : YOSHIMI KOHAYAKAWA

It is certified that error appears in the above-identified patent and that said Letters Patent is hereby corrected as shown below:

ON THE COVER PAGE

<u>At [56]</u>

"L'Esperance" should read -- L'Esperance, Jr. --.

COLUMN 1

Line 20, "a" should be deleted.
Line 23, "such" should read -- such a --.

COLUMN 3

Line 26, "when" should read -- then --.

COLUMN 8

Line 58, "density" should read -- intensity --.
Line 68, "plane;" should read -- plane; and --.

UNITED STATES PATENT AND TRADEMARK OFFICE
CERTIFICATE OF CORRECTION

PATENT NO. : 5,090,798
DATED : February 25, 1992
INVENTOR(S) : YOSHIMI KOHAYAKAWA It is certified that error appears in the above-indentified patent and that said Letters Patent is hereby corrected as shown below:

COLUMN 10

Line 3, "apparatus to" should read --apparatus according to--.

Signed and Sealed this

Eighth Day of June, 1993

Attest:

MICHAEL K. KIRK

*Attesting Officer*     Acting Commissioner of Patents and Trademarks